United States Patent
Kim et al.

(10) Patent No.: US 8,986,758 B2
(45) Date of Patent: Mar. 24, 2015

(54) METHOD FOR EXTRACTING A TRADITIONAL HERBAL MEDICINE COMPONENT USING A POLISHED-RICE STEAMING METHOD

(75) Inventors: Dong Hyun Kim, Suwon-si (KR); Ji Seong Kim, Yongin-si (KR); Hui Kyeung Chang, Yongin-si (KR); Duck Hee Kim, Seoul (KR); Han Kon Kim, Suwon-si (KR)

(73) Assignee: Amorepacific Corporation (KR)

( * ) Notice: Subject to any disclaimer, the term of this patent is extended or adjusted under 35 U.S.C. 154(b) by 57 days.

(21) Appl. No.: 13/511,792

(22) PCT Filed: Nov. 17, 2010

(86) PCT No.: PCT/KR2010/008133
§ 371 (c)(1),
(2), (4) Date: May 24, 2012

(87) PCT Pub. No.: WO2011/065699
PCT Pub. Date: Jun. 3, 2011

(65) Prior Publication Data
US 2012/0251470 A1    Oct. 4, 2012

(30) Foreign Application Priority Data
Nov. 25, 2009  (KR) .................. 10-2009-0114650

(51) Int. Cl.
| | |
|---|---|
| *A61K 36/00* | (2006.01) |
| *A61K 36/16* | (2006.01) |
| *A61K 36/65* | (2006.01) |
| *A61K 36/232* | (2006.01) |
| *A61K 36/24* | (2006.01) |
| *A61K 36/06* | (2006.01) |
| *A61K 8/97* | (2006.01) |
| *A61Q 19/02* | (2006.01) |

(52) U.S. Cl.
CPC .. *A61K 8/97* (2013.01); *A61Q 19/02* (2013.01)
USPC ....... 424/752; 424/725; 424/778; 424/195.15

(58) Field of Classification Search
CPC ....... A61K 9/06; A61K 36/16; A61K 36/076; A61K 36/65; A61K 36/232; A61K 36/24
USPC ..................... 424/750, 752, 195.5, 778, 725
See application file for complete search history.

(56) References Cited

FOREIGN PATENT DOCUMENTS

| | | |
|---|---|---|
| CN | 101062128 A | 10/2007 |
| JP | 61-50909 | 3/1986 |
| JP | 2005-112793 | 4/2005 |
| KR | 92-005683 | 7/1992 |
| KR | 1993-0010548 | 10/1993 |
| KR | 20040078610 A * | 9/2004 |
| KR | 10-0535875 B1 | 12/2005 |
| KR | 10-0654959 B1 | 12/2006 |
| KR | 10-0713718 | 5/2007 |

OTHER PUBLICATIONS

Zhao Lina et al.(Chinese Medicine processing branch 2008 symposium, Association of Chinese Medicine, pp. 148-151).*
Chinese Office Action from corresponding Chinese Patent Application No. 201080053134.X mailed Mar. 4, 2013.
Zhao Lina et al., "Study of history of rice processing method for Chinese herbal medicine", *Chinese medicine processing branch 2008 symposium, Association of Chinese Medicine*, 2008, pp. 148-151.
Office Action from corresponding Chinese Patent Application No. 201080053134.X (mailed Sep. 12, 2013).
Tong et al., "Comparative studies on tyrosinase inhibitory activities of aqueous and ethanolic extracts of cosmetic whitening traditional Chinese medicine," Chin Pharm J, 40(5):P342-343 (Mar. 2005).
International Search Report for International Patent Application No. PCT/KR2010/008133 (Aug. 1, 2011).
Kim et al. "The Whitening Effect of *Angelicae dahuricae* Radix Water Extract in Brown Guinea Pigs." *J. Env. Hlth. Sci.*, 35(5):417-25 (2009).
Kim et al., "The Whitening Effect of *Angelicae dahuricai* Radix Water Extract in Brown Guinea Pigs," *J. Env. Hlth. Sci.*, 35(5):P417-425 (2009).
Makoto, "Processing of material." *Modern Oriental Med.*, 5(3) P112-113 (1984).

* cited by examiner

*Primary Examiner* — Chris R Tate
*Assistant Examiner* — Deborah Davis
(74) *Attorney, Agent, or Firm* — Merchant & Gould P.C.

(57) ABSTRACT

Disclosed are: a method for extracting a traditional herbal medicine component comprising a process in which a traditional oriental medicine component is steamed together with polished rice; and a composition for an external application to skin comprising an extract which has been extracted by means of the method. The component extracted by means of the extraction method reduces the cytotoxicity of the traditional oriental medicine, is recognized as being effective in alleviating skin irritation, and exhibits an outstanding skin-whitening effect.

7 Claims, 2 Drawing Sheets

CONTROL    COMP. EX. 1    EX. 1

CONTROL    COMP. EX. 2    COMP. EX. 3

METHOD FOR EXTRACTING A TRADITIONAL HERBAL MEDICINE COMPONENT USING A POLISHED-RICE STEAMING METHOD

This application is a U.S. National Stage Application under 35 U.S.C. §371 of International Patent Application No. PCT/KR2010/008133, filed 17 Nov. 2010, which claims the benefit of priority to Korean Patent Application No. 10-2009-0114650 filed 25 Nov. 2009, the disclosures of all of which are hereby incorporated by reference in their entireties. The International Application was published in Korean on 3 Jun. 2011 as WO 2011/065699.

TECHNICAL FIELD

The present disclosure relates to a method for extracting a traditional herbal medicine component using a polished-rice steaming method, and a composition for an external application to skin containing a component which has been extracted by the method.

BACKGROUND

Human skin colors are determined by amounts of melanin, carotene and hemoglobin. Among those, melanin plays the most important role. Melanin is produced via enzymatic or non-enzymatic oxidation of tyrosine at cells called melanocytes present at the stratum basale of epidermis, and transferred to keratinocytes forming the epidermis.

Melanin pigment produced at skin melanin cells is a phenolic polymer substance in the form of a complex of black pigment with protein. Such melanin pigments play an important role in inhibiting skin damages caused by ultraviolet rays irradiated from the sun. However, excessive synthesis and accumulation of melanin causes severe aesthetic skin troubles, such as freckles, ephelides and senile plaques, stimulates skin aging or causes skin cancers. It is known that the most important factor in biosynthesis of melanin is functions of tyrosinase present at melanin cells. Thus, most studies about skin whitening and skin cancer prevention through inhibition of excessive production and deposition of melanin are focused on inhibition of tyrosinase activities. Many compounds having tyrosinase-inhibiting activity have been used as materials for whitening cosmetics. However, they are limited in practical application, because they have poor stability to cause decomposition and coloring, generate off-flavors, have unclear effects in bio-level and are problematic in terms of stability.

Therefore, to prevent and overcome such problems, many studies and technological development have been conducted by searching for herb medicines having relatively low toxicity and excellent whitening activity. For example, there are known Korean Patent Publication No. 1993-0010548 (Whitening Cosmetics Containing *Broussonetia* Extract), Korean Patent No. 10-0535875 (Cosmetic Composition Containing Mixed Plant Extract Having Skin Whitening Effect), Korean Patent No. 10-0654959 (Skin Whitening Cosmetic Composition). However, disclosures of the above patent documents cause problems of skin irritation and toxicity due to the use of herb medicines, and thus are not amenable to skin applications at high concentrations. In addition, when the compositions according to the related art are applied at reduced concentrations, they provide insufficient whitening effects.

SUMMARY OF THE INVENTION

Technical Problem

The present disclosure is directed to providing a method for extracting a traditional herbal medicine component, which reduces cytotoxicity.

The present disclosure is also directed to providing a cosmetic composition causing little skin irritation and having an excellent whitening effect.

Technical Solution

In one aspect, there is provided a method for extracting a traditional herbal medicine component, comprising a process in which a traditional oriental medicine component is steamed together with polished rice. In another aspect, there is provided a composition for an external application to skin including the extract obtained by the method.

Advantageous Effects

The traditional herbal medicine component extracted by the method disclosed herein is recognized as being effective in reducing cytotoxicity and alleviating skin irritation. In addition, the composition for an external application to skin including the extract obtained by the method exhibits an outstanding skin-whitening effect and may be applied to various industrial fields including cosmetic industry.

DETAILED DESCRIPTION

Figure 1:
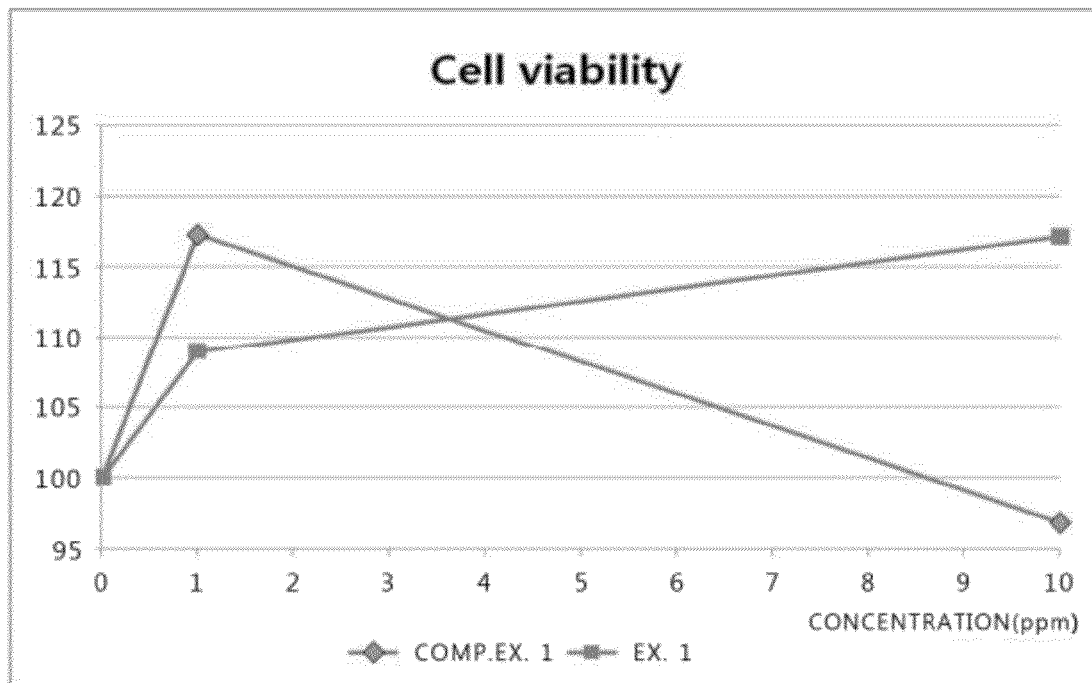
FIG. 1 and FIG. 2 are graphs illustrating the comparative results of cell viability after treating cells with the extract of traditional herbal medicine component according to an embodiment.

In one aspect, there is provided a method for extracting a traditional herbal medicine component, including a process in which a traditional oriental medicine component is steamed together with polished rice. Through the process of steaming with polished rice, it is possible to remove toxicity contained in the traditional oriental medicine and to alleviate skin irritation.

According to an embodiment, the traditional oriental medicine is not particularly limited, and may be at least one selected from the group consisting of *Angelica dahurica* Bentham, *Cynanchum wilfordii* Hemsley, *Ginkgo biloba* Hibiscus, *Poria cocos* and *Paeonia lactiflora*. After steaming the traditional oriental medicine together with polished rice, the resultant component has significantly reduced cytotoxicity and shows an excellent skin whitening effect.

According to an embodiment, the process in which the traditional oriental medicine component is steamed together with polished rice may include exposing the traditional oriental medicine component and polished rice to hot water steam, or heating the traditional oriental medicine component and polished rice dipped in water. For example, the process in which the traditional oriental medicine component is steamed together with polished rice may be carried out by cooking rice from the traditional oriental medicine component and polished rice.

According to an embodiment, the method for extracting a traditional herbal medicine component may further include extracting the traditional oriental medicine component, after the traditional oriental medicine component is steamed together with polished rice. The process of extracting the traditional oriental medicine component may be carried out in a manner generally known to those skilled in the art. For example, water or an organic solvent is added to the traditional oriental medicine component steamed together with polished rice, carrying out extraction under flux to form precipitate, carrying out filtration using a filter and centrifugal separation to separate the residue from the filtrate, and concentrating the separated filtrate under reduced pressure to obtain extract of the traditional oriental medicine.

According to another embodiment, the method for extracting a traditional herbal medicine component may further include extracting the traditional oriental medicine component via solvent extraction, after the traditional oriental medicine component is steamed together with polished rice. There is no particular limitation in the solvent used for such solvent extraction and particular examples of the solvent include water, an organic solvent or a mixture thereof. More particularly, the solvent may be selected from ethanol, methanol, butanol, ether, ethyl acetate, chloroform or a mixture of water with any one of them. The solvent may be ethanol, more specifically 80% ethanol.

The solvent extraction may be carried out at a temperature of 10-80° C. for 6-24 hours. Although there is no particular limitation in extraction conditions, temperatures or times beyond the above-specified range may cause a drop in extraction efficiency or degeneration of the component.

The extract obtained by the solvent extraction of the traditional oriental medicine component may be subjected to further processing. For example, the extract obtained by the solvent extraction may be subjected to macerating or heating at room temperature, followed by filtering, to obtain a liquid product, which, in turn, may be subjected to solvent evaporation, spray drying or freeze drying.

In another aspect, there is provided a traditional herbal medicine component-containing composition for an external application to skin, including the extract obtained by the method for extracting a traditional herbal medicine component disclosed herein. Particularly, the composition for an external application to skin including the traditional herbal medicine component extracted through the process of steaming the traditional oriental medicine together with polished rice is effective for reducing toxicity and alleviating skin irritation.

According to an embodiment, the traditional herbal medicine component-containing composition for an external application to skin may be a cosmetic composition.

According to another embodiment, the cosmetic composition may be a skin whitening composition. The traditional herbal medicine component as an active ingredient of the composition disclosed herein inhibits melanin production to provide an excellent skin whitening effect. The traditional herbal medicine component contained in the cosmetic composition is not particularly limited. For example, the traditional herbal medicine component may be present in the composition in an amount of 0.001-90 wt %, particularly 0.01-30 wt %, more particularly 0.1-10 wt % based on the total weight of the composition. The above-defined range is intended to improve a whitening effect. Thus, any amount lower than the above-defined range may not provide a sufficient skin whitening effect. In addition, even if the component is present in an amount exceeding the above-defined range, it may provide no improvement in whitening effect despite extra addition of the active ingredient.

When the composition for an external application to skin disclosed herein is to be formulated into cosmetics, it may be provided as one or more formulations selected from the group consisting of skin softeners, astringent, nourishing lotion, eye cream, nourishing cream, massage cream, cleansing cream, sun cream, cleansing foam, cleansing water, powder, essence, foundation, makeup base or pack, but is not limited thereto.

MODE FOR INVENTION

The examples and test examples will now be described. The following examples and test examples are for illustrative purposes only and not intended to limit the scope of the present disclosure.

COMPARATIVE EXAMPLE 1

Preparation of Extract of Traditional Herbal Medicine

To commercially available *Angelica dahurica* Bentham, *Cynanchum wilfordii* Hemsley, *Ginkgo biloba Hibiscus, Poria cocas* and *Paeonia lactiflora* (each 300 g, total 1.5 kg), 7 L of 80% aqueous ethanol solution is added. Then, the resultant mixture is extracted under reflux three times and allowed to precipitate at 15° C. for 1 day. After that, filtration using a filter and centrifugal separation are carried out to separate the residue from the filtrate, and the separated filtrate is concentrated under reduced pressure to obtain 86 g of extract of a traditional herbal medicine.

EXAMPLE 1

Preparation of Extract of Traditional Herbal Medicine Using Polished Rice

First, 4 L of water is added to 2 kg of polished rice and cooked at a high heat. When the ricewater is on the verge of boiling-over, commercially available *Angelica dahurica* Bentham, *Cynanchum wilfordii* Hemsley, *Ginkgo biloba Hibiscus, Poria cocas* and *Paeonia lactiflora* (each 300 g, total 1.5 kg), wrapped with hemp cloth, are introduced to the center of polished rice, followed by heating at a low heat for about 1 hour. After heating, the traditional herbal medicines are recovered and 7 L of 80% aqueous ethanol is introduced thereto. Then, the resultant mixture is extracted under reflux three times and allowed to precipitate at 15° C. for 1 day. After that, filtration using a filter and centrifugal separation are carried out to separate the residue from the filtrate, and the separated filtrate is concentrated under reduced pressure to obtain 95 g of extract of a traditional herbal medicine.

TEST EXAMPLE 1

Cell Viability Test

The extract of a traditional herbal medicine obtained from Example 1 is subjected to a cell viability test. Example 1 represents extract of a traditional oriental medicine component treated with the polished-rice steaming method disclosed herein, while Comparative Example 1 represents extract of a traditional herbal medicine according to the related art using no polished-rice steaming method. In addition, Comparative Example 2 represents the residue remaining after extracting the extract of a traditional herbal medicine according to Example 1. Comparative Example 3 represents a sample obtained by steaming polished rice alone. Each sample according to Example 1 and Comparative Examples 1-3 is tested for cell viability. The results are shown in FIG. 1 and FIG. 2.

Referring to FIG. 1, as compared to Comparative Example 1, Example 1 provides significantly increased cell viability as a function of concentration of extract in a concentration-dependent manner. In addition, referring to FIG. 2, Comparative Example 2 representing the residue remaining after extracting the extract of a traditional herbal medicine according to Example 1 shows little change in cell viability as a function of concentration. In the case of Comparative Example 3 representing a sample obtained by steaming polished rice alone, it is shown that cell viability increases as a function of concentration.

Figure 2:
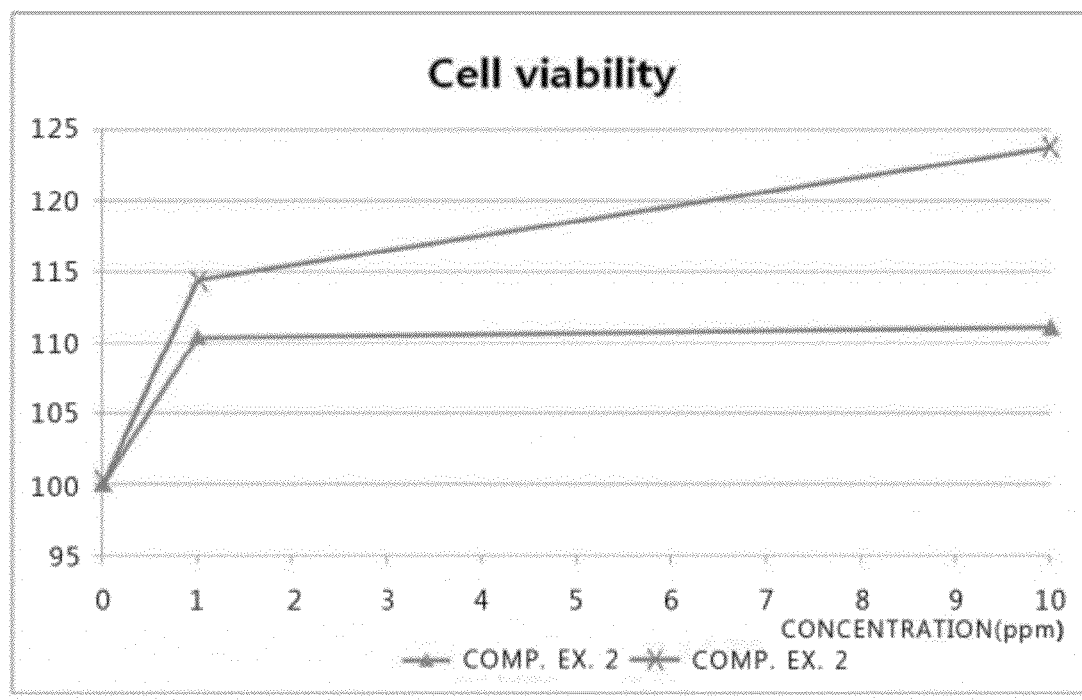

As can be seen from FIG. 1 and FIG. 2, toxic ingredients are removed from traditional oriental medicine components by way of the polished-rice steaming method disclosed herein.

TEST EXAMPLE 2

Cell Morphology Test

Figure 3:
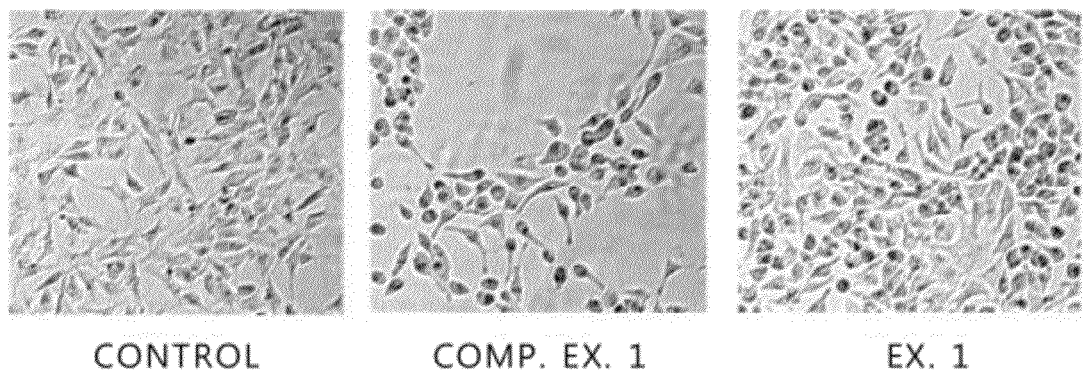
FIG. 3 and FIG. 4 show the comparative results of cell morphology tests observed by electron microscopy after treating samples with the extract of traditional herbal medicine component according to an embodiment.
Figure 4:
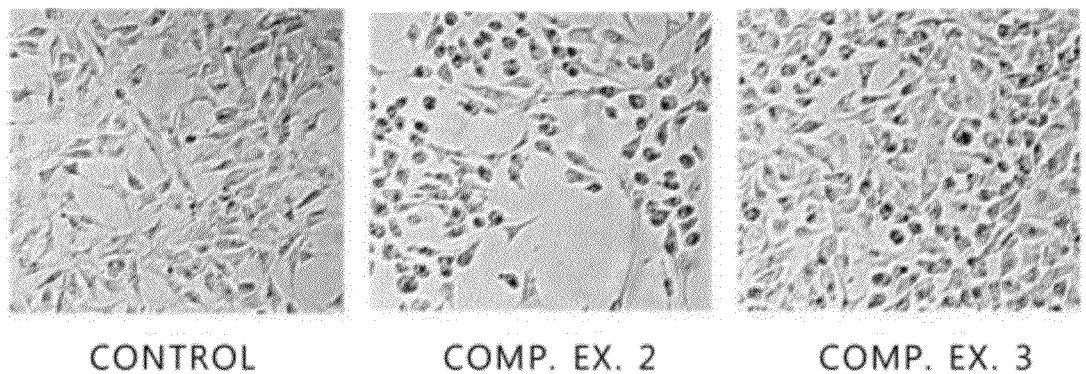

The samples are observed by electron microscopy to determine cell morphology after they are subjected to the cell viability test according to Test Example 1. The results are shown in FIG. 3 and FIG. 4. In FIG. 3 and FIG. 4, the vacancies represent dead cell portions.

Therefore, the number of destroyed cells is in proportion to the vacancies. In addition, the sharp portions represent differentiation of damaged cells.

In this test, Example 1 represents extract of a traditional oriental medicine component treated with the polished-rice steaming method disclosed herein, while Comparative Example 1 represents extract of a traditional herbal medicine according to the related art using no polished-rice steaming method. In addition, Comparative Example 2 represents the residue remaining after extracting the extract of a traditional herbal medicine according to Example 1. Comparative Example 3 represents a sample obtained by steaming polished rice alone. As a control, non-treated samples are subjected to the cell morphology test.

TEST EXAMPLE 3

Determination of Effect of Inhibiting Melanin Production Using Mouse Pigment Cells C57BL/6 mouse-derived pigment cells (Mel-Ab cells) (Dooley, T. P. et al., Skin pharmacol, 7, pp. 188-200) are cultured in a DMEM (Eagle's minimal essential medium), to which 10% fetal bovine serum, 100 nM 12-O-tetradecanoylphorbol-13-acetate and 1 nM cholera toxin are added, at 37° C. under 5% $CO_2$. The cultured Mel-Ab cells are released by using 0.25% trypsin-EDTA and incubated on a 24-well plate at a concentration of $10^5$ cells/well. From the next day, each test sample is added to culture the cells continuously for 3 days.

The test samples used herein include hydroquinone, the extract of traditional herbal medicine of Comparative Example 1 and the extract of traditional herbal medicine obtained by polished-rice steaming method according to Example 1. Each sample is used at a concentration of 10 ppm. Hydroquinone is used as a positive control. Then, the culture medium is removed and the cells are washed with phosphate buffered saline (PBS). The cells are subjected to cell lysis using 1N sodium hydroxide and absorbance is determined at 400 nm. The absorbance measurement is used to calculate % inhibition of melanin production according to the following Mathematical Formula 1. The results are shown in the following Table 1 (Dooley's method).

% Inhibition of melanin production=100−{(absorbance of each sample/absorbance of control)× 100}     [Mathematical Formula 1]

TABLE 1

| Test sample | % inhibition of melanin production |
|---|---|
| Non-treated (control) | 0 |
| Comp. Ex. 1 | 22.1 |
| Ex. 1 | 55.2 |
| Hydroquinone (positive control) | 58.9 |

As can be seen from Table 1, the extract of traditional herbal medicine obtained by the polished-rice steaming method disclosed herein provides % inhibition of melanin production similar to hydroquinone, a known whitening active material.

TEST EXAMPLE 4

Irritation Test

The extract of traditional herbal medicine according to Example 1 is tested for irritation as compared with kojic acid, a known whitening active material. Particularly, 15 panels sensitive to irritation, such as stinging, burning, etc., are subjected to a test for determining irritation feeling, including stinging, itch and dazzling.

Each test panel is allowed to apply 0.5 mL of each of kojic acid (available from YM Chemical Co.) and the extract of traditional herbal medicine according to Example 1 onto his/her skin randomly at the left side or right side, and then evaluate the test sample by grading from 0 to 3.0 at an interval of 0.1. The results are shown in the following Table 2.

<Evaluation Criteria>
0-0.4: No irritation
0.5-1.0: slight irritation
1.1-2.0: mild irritation
2.1-3.0: severe irritation

TABLE 2

|  | Kojic acid | Extract of traditional herbal medicine (Ex. 1) |
|---|---|---|
| Stinging | 0.85 | 0.20 |
| Burning | 0.50 | 0.50 |
| Average | 0.68 | 0.35 |

Referring to Table 2, kojic acid causes slight stinging and burning and a perceptible degree of irritation. On the contrary, the extract of traditional herbal medicine obtained by using the polished-rice steaming method disclosed herein causes a slight degree of burning but substantially imperceptible stinging. As a result, it is shown that the extract of Example 1 causes little irritation on average.

Therefore, since the extract of traditional herbal medicine obtained by using the polished-rice steaming method disclosed herein causes little irritation unlike kojic acid, it provides better applicability than kojic acid.

Hereinafter, some formulation examples will be explained but the following formulation examples are for illustrative purposes only and not intended to limit the scope of the present disclosure.

FORMULATION EXAMPLE 1

Nourishing Milk

Nourishing milk is obtained in a conventional manner according to the composition as shown in the following Table 3

TABLE 3

| Ingredient | Amount (wt %) |
| --- | --- |
| Extract of traditional herbal medicine using polished rice | 5.0 |
| Squalane | 5.0 |
| Bees wax | 4.0 |
| Polysorbate 60 | 1.5 |
| Sorbitane sesquioleate | 1.5 |
| Liquid paraffin | 0.5 |
| Caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, pigment and fragrance | q.s. |
| Purified water | Balance |
| Total | 100 |

FORMULATION EXAMPLE 2

Nourishing Cream

Nourishing cream is obtained in a conventional manner according to the composition as shown in the following Table 4.

TABLE 4

| Ingredient | Amount (wt %) |
| --- | --- |
| Extract of traditional herbal medicine using polished rice | 5.0 |
| Polysorbate 60 | 1.5 |
| Sorbitan sesquioleate | 0.5 |
| PEG60 Cured castor oil | 2.0 |
| Liquid paraffin | 10.0 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Preservative, pigment and fragrance | q.s. |
| Purified water | Balance |
| Total | 100 |

FORMULATION EXAMPLE 3

Massage Cream

Massage cream is obtained in a conventional manner according to the composition as shown in the following Table 5.

TABLE 5

| Ingredient | Amount (wt %) |
| --- | --- |
| Extract of traditional herbal medicine using polished rice | 5.0 |
| Bees wax | 10.0 |
| Polysorbate 60 | 1.5 |
| Sorbitan sesquioleate | 0.8 |
| PEG60 Cured castor oil | 2.0 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Preservative, pigment and fragrance | q.s. |
| Purified water | Balance |
| Total | 100 |

FORMULATION EXAMPLE 4

Pack

Pack is obtained in a conventional manner according to the composition as shown in the following Table 6.

TABLE 6

| Ingredient | Amount (wt %) |
| --- | --- |
| Extract of traditional herbal medicine using polished rice | 5.0 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG12 Nonyl phenyl ether | 0.3 |
| Polysorbate 60 | 0.3 |
| Preservative, pigment and fragrance | q.s. |
| Purified water | Balance |
| Total | 100 |

While the present disclosure has been described with respect to the specific embodiments, it will be apparent to those skilled in the art that various changes and modifications may be made without departing from the spirit and scope of the disclosure as defined in the following claims.

We claim:

1. A method for skin-whitening comprising transdermally administering an effective amount of a composition consisting essentially of a traditional herbal medicine component steamed together with polished rice to a subject in need thereof,
wherein the traditional herbal medicinie component consists of *Angelica dahurica Bentham, Cynanchum wilfordii Hemsley, Ginkgo biloba Hibiscus, Poria cocos* and *Paeonia lactiflora*.

2. The method according to claim 1, wherein the traditional herbal medicine component steamed together with polished rice is obtained by a process comprising exposing the traditional herbal medicine component and polished rice to hot water steam, or heating the traditional herbal medicine component and polished rice dipped in water.

3. The method according to claim 1, wherein the traditional herbal medicine component is obtained by further extracting the traditional herbal medicine component, after the traditional herbal medicine component is steamed together with polished rice.

4. The method according to claim 3, wherein said extracting the traditional herbal medicine component is carried out by solvent extraction using any one of water, an organic solvent or a mixture thereof.

5. The method according to claim 4, wherein the organic solvent is at least one selected from the group consisting of ethanol, methanol, butanol, ether, ethyl acetate, and chloroform.

6. The method according to claim 3, wherein said extracting the traditional herbal medicine component is carried out at a temperature of 10-80° C.

7. The method according to claim 3, wherein said extracting the traditional herbal medicine component is carried out for 6-24 hours.

* * * * *